United States Patent [19]
Rounbehler et al.

[11] Patent Number: 5,300,758
[45] Date of Patent: Apr. 5, 1994

[54] VAPOR DETECTION WITH HIGH SPEED GAS CHROMATOGRAPHY

[75] Inventors: David P. Rounbehler, Bedford; David P. Lieb; Eugene K. Achter, both of Lexington; David B. Gernes, Watertown; Abdul Tafreshi, Lowell, all of Mass.

[73] Assignee: Thermedics Inc., Woburn, Mass.

[21] Appl. No.: 825,368

[22] Filed: Jan. 24, 1992

Related U.S. Application Data

[60] Division of Ser. No. 594,267, Oct. 3, 1990, Pat. No. 5,108,705, which is a continuation-in-part of Ser. No. 491,994, Mar. 12, 1990, abandoned.

[51] Int. Cl.⁵ .............................................. H05B 1/02
[52] U.S. Cl. ..................................... 219/497; 219/499; 219/505; 219/413; 219/491; 73/23.25
[58] Field of Search ............... 219/494, 497, 501, 505, 219/485, 483, 491, 412, 413, 499; 73/23.25

[56] References Cited

U.S. PATENT DOCUMENTS

| | | | |
|---|---|---|---|
| 4,162,379 | 7/1979 | Sebens et al. | 219/497 |
| 4,514,619 | 4/1985 | Kugelman | 219/483 |
| 4,549,073 | 10/1985 | Tamura et al. | 219/497 |
| 4,638,960 | 1/1987 | Straube et al. | 219/497 |
| 4,695,709 | 9/1987 | Sachs et al. | 219/497 |
| 4,705,937 | 11/1987 | Marek | 219/501 |
| 4,805,441 | 2/1989 | Sides et al. | 73/23 |
| 4,923,486 | 5/1990 | Rubey | 55/67 |
| 5,098,451 | 3/1992 | Rounbehler et al. | 55/67 |

OTHER PUBLICATIONS

Hail et al, "Compact Gas Chromatograph Probe For Gas Chromatograph/Mass Spectrometry Utilizing Resistively Heated Aluminum-Clad Capillary Columns", *Anal. Chem.* 1989, vol. 61, Nov. 1, 1989, pp. 2410-2416.

*Primary Examiner*—Mark H. Paschall
*Attorney, Agent, or Firm*—Herbert Messenger

[57] ABSTRACT

Disclosed are a method and apparatus for high speed, selective detection of vapors of specific compounds, particularly nitrogen-containing compounds, utilizing a bypass branch and high speed gas chromatography for improved selectivity and sensitivity of detection. A system with two gas chromatographs (GC's) alternating in series with two pyrolyzers provides two time intervals of detection in a downstream detector, with the second time interval containing signals delayed and further separated relative to signals from the first time interval. The bypass branch, in diverting a portion of the flow of gas samples from passage through the second gas chromatograph and second pyrolyzer, avoids interferences in the first time interval of detection from non-GC-retained compounds decomposed in the second pyrolyzer. Also disclosed is an arrangement for rapid, precise heating of vapor concentrator tubes in which vapors are rapidly focussed and then injected into a GC, and for rapid, precise heating of the GC's.

8 Claims, 4 Drawing Sheets

VAPOR DETECTION WITH HIGH SPEED GAS CHROMATOGRAPHY

Some of the material disclosed and claimed herein was developed with support of the U.S. Government under Contract No. 2038-563371 awarded by the U.S. Department of State. The Government has certain rights in this invention.

CROSS REFERENCE TO RELATED APPLICATION

This is a divisional of copending application Ser. No. 07/594,267 now U.S. Pat. No. 5,108,705 filed Oct. 3, 1990, which is a continuation-in-part of application Ser. No. 07/491,994 filed Mar. 12, 1990, now abandoned.

BACKGROUND OF THE INVENTION

This invention relates to selective detection of vapors and more particularly to improved high speed gas chromatographic analyses for detecting vapors of specific compounds, especially certain nitrogen-containing compounds.

Chromatography is commonly utilized to provide timewise separation of constituents of gas or liquid samples as part of analyses in which specific compounds are detected. The timewise separation achieved among constituents permits particular compounds to be distinguished from potential interferents and from other specific compounds of interest by signal peaks which occur at distinct times as the output of detectors downstream of the gas or liquid chromatograph. The times of interest, and amplitude and even shape of the signals of interest, can be predetermined by calibrations using samples of known composition, and detection systems containing the chromatographs can be electronically programmed to provide alarms of specific responses upon detection of each compound of interest.

Gas chromatographic (GC) systems have proven quite useful in analysis of samples containing vapors or gases of unknown composition. Recently-developed GC systems can separate and detect certain substances within a sample rather quickly and accurately. However, further improvements are desirable, particularly in the selectivity and sensitivity of such GC systems.

Accordingly, it is an object of the invention to provide as improved high speed vapor detection GC system and method.

It is an object of the invention to provide an improved system for selectively detecting specific nitrogen-based compounds.

It is an object of the invention to provide a high speed GC vapor detector which detects different sets of compounds during multiple time intervals and which time shifts the detection of at least one set.

It is a particular object of the invention to provide a high speed vapor detector configured to detect different compounds during two discrete intervals of time and having improvements which eliminate potential interferents during at least one of the detection intervals.

It is also an object of the invention to provide a highly selective and sensitive apparatus and method for improved high speed detection of vapors of nitro-compounds such as explosives.

It is also an object of the invention to provide a method and apparatus for rapidly and precisely controlling the temperature of current-carrying elements such as metal tube casings of components of a high speed GC vapor detector.

SUMMARY OF THE INVENTION

The invention is an improved method and apparatus for high speed, selective detection of vapors of specific compounds. The apparatus has a first gas chromatograph (GC1), a first pyrolyzer, a second gas chromatograph (GC2), and a second pyrolyzer connected successively in series for processing a gas sample containing vapors of compounds to be detected such as nitrogen-containing explosives.

According to one aspect of the invention a flow splitter is provided for directing a portion of the effluent of the first gas chromatograph through a bypass branch rather than into the second gas chromatograph. The portion of gas sample diverted into the bypass branch flows through a third pyrolyzer and into a specific gas detector. The remaining portion is, by action of a valve, either passed into the specific gas detector, preferably in combination with the flow from the bypass branch, or is vented through a vacuum pump. Rapid heating of the gas chromatographs at successive intervals of time, with the valve switched to different positions, permits detection of the specific gas at predetermined times and hence identification of compounds from which the specific gas was produced.

In a preferred detection system two series-connected vapor concentrators VC1 and VC2 are positioned ahead of the first gas chromatograph GC1 to permit rapid concentration of vapors. Concentration, GC injection, and separation of vapors are achieved at high speed by electrical circuitry which provides rapid, precise heating of VC1, VC2, GC1, and GC2. In association with a computer, the control circuit senses resistance of small diameter metal tubes of the vapor concentrators and gas chromatographs as voltage is applied and current is flowed through the tubes to heat vapors therein. At very closely-spaced intervals (e.g., 10 millisecond intervals) power input/tube current is adjusted to achieve desired tube resistances (hence tube temperatures) according to resistance values stored in the computer. In this way rapid, precise profiles of tube temperature with time are achieved to rapidly focus, move, and separate vapors included in gas samples.

In the detection of specific nitrogen-containing compounds such as certain explosives, vapors of nitrogen-containing compounds are directed along with a carrier gas into the first gas chromatograph for separation. The first pyrolyzer is heated to a temperature such that separated vapors of nitramines and nitrite esters, if present in a gas sample passed through the first pyrolyzer in a first time interval as a result of, and typically during, rapid heating of the first gas chromatograph, decompose to produce nitric oxide (NO) gas and nitrogen dioxide ($NO_2$) gas. The $NO_2$ gas in the portion diverted into the bypass branch is converted to NO in the third pyrolyzer, without producing additional NO or $NO_2$ from other compounds which might interfere with detection of compounds from which the NO and $NO_2$ was generated in the first pyrolyzer. NO gas from the bypass branch then is rapidly detected in the NO detector without risk of interferences from decomposition of compounds in the high temperature second pyrolyzer, whose effluent is vented through a vacuum pump during the first time interval. The resulting NO signals from the detector are used to identify specific nitrogen-containing compounds. Both selectivity and sensitivity of detection of nitrogen-containing compounds in the first time interval are increased over results obtained without the bypass branch.

During a second time interval the second gas chromatograph (GC2) is rapidly heated, and separated vapors released from GC2 are decomposed in the second (higher temperature) pyrolyzer to produce NO from nitrogen-containing compounds to be detected. The effluent of the second pyrolyzer, either alone or combined with the effluent of the bypass branch, is directed to the NO detector and the resulting NO signals at predetermined times during the second time interval indicate the presence and identity of the nitrogen-containing compounds from which the NO was produced in the second pyrolyzer.

In a preferred vapor detection system according to the invention the flow splitter for diverting part of the effluent from GC2 to the bypass branch is a simple "T" connection between the first pyrolyzer and the second gas chromatograph. The bypass branch also includes a flow controller such as a length of tubing whose resistance helps determine the fraction of flow passing through the bypass branch. The third pyrolyzer desirably includes gas-contacting surfaces containing silver. A preferred version comprises a silver tube, and is operable at a relatively low temperature—e.g., in the range of about 140° C. to 200° C.—to reduce $NO_2$ to NO without producing NO from other vapors of nitrogen-containing compounds which could interfere with detection of the specific compounds to be detected during the first time interval.

DESCRIPTION OF PREFERRED EMBODIMENTS

Figure 1:
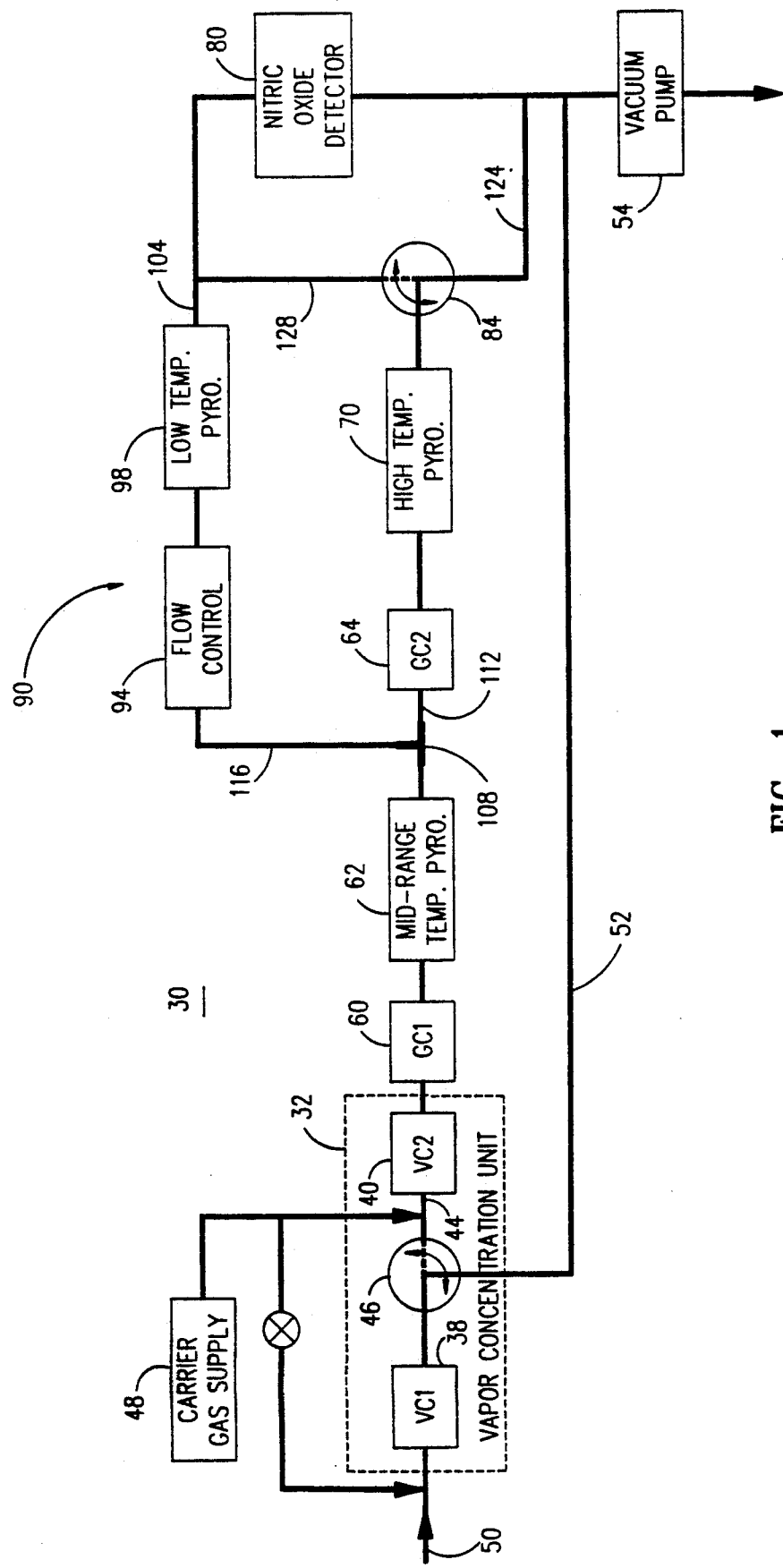
FIG. 1 is a block diagram of a vapor detection system according to a preferred embodiment of the invention.

FIG. 1 is a block diagram illustrating the major components of an improved vapor detection system 30 according to the present invention. The system 30 is shown as including a detector for nitrogen-containing compounds, particularly those containing one or more $NO_2$ groups such as nitrogen-based explosives. However, its principles are applicable to other compounds through the use of specific gas detectors other than NO detectors.

The system 30 includes several series-connected components through which vapors contained in a gas sample are directed. The vapors are successively concentrated, separated in gas chromatographs, and heated in pyrolyzers to produce specific gases. Detection of the specific gases such as nitric oxide (NO) at distinct times in turn permits detection of the compounds from which the gas was produced.

As used herein, the term "vapors" means materials not only in the gas phase but also in the form of aerosols and fine suspensions of particles. Such vapors may be present in ambient air in minute quantities (e.g., 0.1 parts explosives per trillion parts air or less) or readily stripped from surfaces and collected by passing air over the surface with or without heating and/or contacting the surface with air jets. The vapors of interest for detection according to the present invention are those which may be selectively retained and separated in high speed gas chromatographs. The term "gas sample" is used herein to refer a mixture of vapors and either air or another carrier gas (e.g., hydrogen or helium).

An understanding of the benefits provided by the vapor detection system 30 and particularly by its bypass branch is facilitated by knowledge of the operation of its series-connected, dual arrangements of gas chromatographs and pyrolyzers. It should be kept in mind in the following explanation of those components that an important feature of the system 30 is its capability of rapidly analyzing samples—e.g., in about thirty seconds or less (ten seconds or less beginning with the injection of a sample into its first gas chromatograph).

Initially, gas samples to be analyzed for the presence of specific vapors such as nitrogen-based explosives (e.g., TNT, nitroglycerin) may contain vapors at concentrations too low for rapid, accurate analyses. Accordingly, the vapor detection system 30 desirably includes a vapor concentration unit 32 which traps and concentrates vapors from a flow of air or carrier gas passed through it. As illustrated in FIG. 1, a preferred vapor concentration unit 32 comprises two vapor concentrators VC1 38 and VC2 40 connected by a flow line 44 in which a valve 46 is provided. Each of the vapor concentrators VC1 38 and VC2 40 is connected to a carrier gas supply 48 which supplies to the concentrators a gas such as hydrogen. The vapor concentration unit 32 is typically operated by first passing an air sample (a sample which may have been produced by first trapping vapors in a collector then desorbing vapors into a flow of air passed through the collector) along an inlet flow line 50 into the VC1 38, with the effluent of VC1 38 (air and non-trapped constituents) being passed along an exhaust line 52 to a vacuum pump 54. In this way vapors which are constituents of the air sample are trapped in VC1 38. The valve 46 is then switched to permit flow communication between the VC1 38 and the VC2 40 (which may be of smaller internal volume). Vapors are then flashed from the VC1 38 by an abrupt heating of VC1 38 and are carried by carrier gas from the supply 48 into the VC2 40 where they are trapped and thus further concentrated.

Preferred vapor concentrators of the detection system 30 each include a small diameter tube such as, in the case of VC1 38 and VC2 40, a 0.32 mm ID quartz capillary GC tube about 5 inches in length and whose inner surface has a thin coating (e.g., 1-3 microns) of a gas chromatographic material such as polymerized silicone (e.e. DB 5 available from J&W Scientific of Folsom, Calif.). In effect, each concentrator is a short gas chromatograph tube. The capillary tube is threaded through, or tightly encased in, a needlestock metal tube whose outer surface is in thermal contact with a cooled mass. This mass—e.g., a block of metal in thermal contact with a thermoelectric cooler and with the metal tube, but electrically insulated from the metal tube by one or more layers of insulation such as silicone rubber wrapped around the metal tube—normally maintains the metal tube, and hence inner capillary tube, of the vapor concentrator 38 or 40 at or below room temperature (e.g., at a temperature such as about 10° C.) so that the GC coating will trap vapors from gas samples directed through the capillary tube. The outer metal tube is also connected to a source of electric power for controlled, very rapid resistance heating of the metal tube—for example, from about 10° C. to 250° C. in about one second. This very rapid heating, preferably accomplished automatically under programmed control in which (as described below) resistance of the tube is continually monitored and employed as a feedback parameter in controlling the power applied to the tube and hence the temperatures attained, in turn heats the GC coating within the capillary tube to release or flash the vapors into a flow of carrier gas directed through the capillary tube. Such carrier gas may in certain applications be air, a principal advantage of which is its ready availability. However, air has been found less suitable than other gases for analyses of nitrogen-containing compounds requiring high sensitivity, selectivity, and speed because of its impurities and relatively high molecular weight, and because its oxygen content may foster undesirable reactions. Preferred carrier gases are those which are pure, lightweight, and non-reactive with the compounds to be detected or with their thermal decomposition products or with other compounds which are likely to be present in gas samples. Hydrogen, furnished under pressure to the vapor concentrator 38 or 40 from the carrier gas supply 48, is a preferred carrier gas for use in analysis of nitrogen-containing compounds such as explosives. It has been found safe even when flowing (at low pressures) through a chemiluminescence-based NO detector supplied with ozone as one reactant. Helium is also suitable as a carrier gas.

After vapors have been transferred to and trapped within the VC2 40, this vapor concentrator is flash-heated while carrier gas is flowing through VC2 40. Vapors are swept out of VC2 40, without decomposition of compounds of interest, and are rapidly passed or "injected" into a first gas chromatograph 60 (GC1 60). The GC1 selectively retains and separates vapors of specific compounds both from other compounds to be detected and from compounds not of interest.

GC1 60 and a second gas chromatograph 64 (GC2 64) which receives the effluent of GC1 60 after its passage through a mid-range temperature pyrolyzer 62, may have a construction similar to that of the vapor concentrator 38 except they are typically coiled and are substantially longer. Typical lengths of GC1 60 and GC2 64 are two to ten feet. Also, GC1 60 and GC2 64 are preferably maintained at temperatures somewhat higher (e.g., at 80° C. to 120° C.) than the vapor concentrator 38 by ovens (FIG. 3), except for brief intervals when their temperatures are rapidly increased by application of electrical power to the metal tubes encasing their GC capillary columns. When the temperature of GC1 60 is "ramped up"—for example from about 95° C. to 300° C. in a 3–4 second interval, vapors which have been retained and are undergoing timewise separation after being received from the vapor concentrator 38 rapidly emerge in separated form from GC1 60 and pass to the mid-range temperature pyrolyzer 62. The same effect is later produced, by controlled heating of GC2 64, on separable vapors which have been received for selective retention and separation in undecomposed form from the mid-range temperature pyrolyzer 62.

The mid-range temperature pyrolyzer 62 may comprise a short (e.g., six-inch) portion of the (capillary tube) flow line between GC1 60 and GC2 64. The pyrolyzer 62, however, is preferably continuously heated to a temperature sufficient to decompose a first set of specific compounds, if present in the vapors contained in a gas sample, without decomposing vapors of a second set of (more thermally stable) compounds. For example, in the detection of certain nitrogen-containing explosives, the mid-range temperature pyrolyzer 62 may be maintained, as by electrical heating, at a temperature of about 400° C. At this temperature, explosives vapors which are nitramines and nitrite esters (compounds having, respectively, N—NO$_2$ or O—NO$_x$ ($x=1, 2$) in their structural formulas-e.g., nitroglycerin (NG), ethylene glycol dinitrate (EGDN), pentaerythritol tetranitrate (PETN), and the nitramines HMX and RDX—readily decompose to produce nitric oxide (NO) gas and nitrogen dioxide (NO$_2$) gas when passed through the pyrolyzer 62 at flow rates of about one cubic centimeter per second. However, explosives of a second set of compounds known as C-nitro compounds (compounds having C—NO$_x$ ($x=1, 2$) in their structural formulas—e.g., dinitrotoluene (DNT) and trinitrololuene (TNT)) and other organic nitrogen-containing compounds such as perfumes, paint residues, etc. which are potential interferents do not decompose when passed through the pyrolyzer tube 62 as vapors in a carrier gas such as hydrogen.

A high temperature pyrolyzer 70, positioned to receive the effluent of GC2 64, may be of a construction similar to that of the mid-range temperature pyrolyzer 62, or may be a quartz or ceramic tube, typically about five to twelve inches in length and having an inner diameter of about one-eighth inch. The high temperature pyrolyzer 70 is maintained at a temperature in the range of about 800° C. to 1000° C., typically about 850° C., by a heater. At this temperature vapors of the second set of compounds to be detected (e.g., DNT and TNT), as well as the NO$_2$ gas produced by decomposition of vapors in the mid-range temperature pyrolyzer 62, decompose to produce NO when contained in gas samples passed through the high temperature pyrolyzer 70.

Nitric oxide gas produced in either of the pyrolyzers 62 or 70 is monitored in a nitric oxide detector 80 whose inlet is in communication with the outlet of the high temperature pyrolyzer 70 through a valve 84. The nitric oxide detector 80 may be any suitable highly sensitive, high speed NO analyzer such as a detector using principles of electron capture, photoionization, or chemiluminescence. A preferred NO detector 80 is an ozone-based chemiluminescence detector similar to those used in Thermal Energy Analyzers (TEA's) available from Thermedics Inc. of Wildwood Street, Woburn, Mass., U.S.A. in which ozone supplied to a reaction chamber (under vacuum such as 1–10 torr provided by the vacuum pump 54) reacts with NO in a gaseous sample to produce "excited" NO$_2$. Rapid decay of the excited NO$_2$ to NO$_2$ yields radiation detectable by a photodetector. The resulting signals and their times of occurrence permit identification of specific compounds to be detected.

The series-connected, dual GC-pyrolyzer combinations of the vapor detection system 30, permit time-shifting of signals by delaying production (and hence detection) of NO gas by a second set of separable compounds which do not decompose when passed through the mid-range temperature pyrolyzer 62 but do decompose when (later) passed through the high-temperature pyrolyzer 70. This permits NO signals from nitramines and nitrite esters to be generated and appear in a first interval of time prior to the decomposition of other compounds retained in, or slowly migrating through, GC2 64.

The second time interval of detection is initiated by the shifting of the valve 84 and the ramping up of the temperature of GC2 64. Decomposition of these compounds (e.g., C-nitro compounds such as TNT) in the high temperature pyrolyzer 70 results in generation of additional NO signals in the NO detector 80 in a second interval of time.

The time-shifting of signals provided by the vapor detection system 30 is of considerable utility in high speed selective detection of compounds such as explosives since it reduces, for each time interval, the number of signals among which specific compounds must be identified or distinguished. It also increases the separation between certain signals of interest. For example, specific compounds (nitramines, nitrite esters) whose signals appear in the first interval of time are not masked by signals of other compounds which are time-shifted into the second interval of time.

In addition to enhancing the selectivity of detection by shifting signals for certain compounds (i.e., GC-separable compounds other than nitramines and nitrite esters) to a second detection time interval, the vapor detection system 30 provides further improvements in detection over prior art systems. These improvements are best understood by reference to the system 30 without its bypass branch 90, whose components (a flow controller 94 and a low temperature pyrolyzer 98) and function are described below.

One drawback of a system having series-connected, dual GC-pyrolyzer combinations but lacking the bypass branch 90 is that it does not time-shift all signals whose presence could interfere with detection of a specific compounds. In particular, interferences to detection of certain nitrogen-containing compounds such as explosives may arise from compounds which a) are poorly or ineffectively retained on GC1 60 and GC2 64 at their normal operating temperatures, b) do not decompose in passing through the mid-range temperature pyrolyzer 64, and c) do decompose in passing through the high temperature pyrolyzer 70. Such compounds may produce signals which show up as interferences in the first time interval of detection. These interferences can occur if the total time for such compounds (e.g., perfumes, paint additives, nitrobenzenes) to reach the high temperature pyrolyzer 70, and then to reach the detector 80 as NO, is nearly equal to the time of arrival of NO for any of the first set of specific compounds. Moreover, such compounds, in addition to producing signals at specific times which conflict with detection, can generate significant amounts of background noise and restrict the sensitivity of detection to levels below those desired.

Certain of the above-noted interferences could be avoided, at least in part, by introduction of a time delay after passage of a sample into, but prior to the heating of, GC1 60. However, this would be quite undesirable for high speed analyses since such delays would directly increase the overall detection time by the length of the time delay.

The inclusion in the vapor detection system 30 of the invention of the bypass branch 90 avoids such interferences without the need for an additional time delay. The bypass branch 90 diverts a portion (e.g., 60–80%) of the effluent of the mid-range temperature pyrolyzer 62 so that it bypasses the second gas chromatograph GC2 64 and the high temperature pyrolyzer 70. Gases and vapors directed through the bypass branch 90 and which then pass to the nitric oxide gas detector 80 along a flow line 104, because they avoid the high temperatures of the pyrolyzer 70, contain decomposition products only of the mid-range temperature pyrolyzer 62 (as further reacted in the low temperature pyrolyzer 98 of the bypass branch 90). Interferences associated with reaction products of the high temperature pyrolyzer 70 are absent, and the vapor detection system 30 also achieves detection times comparable to those of a system without the bypass branch 90.

Diversion of a portion of the effluent of the mid-range temperature pyrolyzer 62, which includes vapors contained in a carrier gas, to the bypass branch 90 may be accomplished by a simple "T" connection 108 in the flow line 112 between GC2 64 and the mid-range temperature pyrolyzer 62 and the operation of the flow controller 94 communicating with the T 108 through a flow line 116. The flow controller 94 helps regulate the fraction of effluent of the pyrolyzer 62 which passes through the bypass branch 90, and may be merely a coiled capillary tube providing a fixed amount of flow resistance. Alternatively, the controller 94 comprises a valve whose setting may be varied so as to allow different amounts of gas flow through the bypass branch 90.

The low temperature pyrolyzer 98 provided as part of the bypass branch 90 functions primarily to reduce to nitric oxide (NO) any $NO_2$ gas in the effluent received from the mid-range temperature pyrolyzer 62. (This function is also performed by the high temperature pyrolyzer 70 with respect to $NO_2$ gas in a sample passing through the pyrolyzer 70.) A suitable low temperature pyrolyzer 98 is a tube formed of, or containing, silver and operable at a temperature in the range of about 140° C. to 200° C.—e.g., at 180° C. A preferred low temperature pyrolyzer 98 comprises a silver tube about twelve inches in length and having an inner diameter of about 0.075 inches and an outer diameter of about one-eighth inch.

The vapor detection system 30 of FIG. 1 is operated to provide 1) a first time interval of detection tt1 (shown in FIG. 2) in which NO produced in the mid-range temperature pyrolyzer 62 (and also produced by reduction of $NO_2$) is detected as NO in the nitric oxide detector 80 and 2) a second time interval of detection tt2 in which NO produced in the high temperature pyrolyzer 70 is detected in the nitric oxide detector 80. To control the flow of sample gas to the NO detector 80, the valve 84 downstream of the high temperature pyrolyzer 70 is set so that during the first time interval tt1 flow of effluent from the high temperature pyrolyzer 70 passes only to the vacuum pump 54 along a flow line 124. Hence during interval tt1 NO signals from the nitric oxide detector 80 represent NO produced only by decomposition of nitramines and nitrite esters in the mid-range temperature pyrolyzer 62 (and NO from reduction of $NO_2$ by the low temperature pyrolyzer 98). At the end of the first time interval tt1 the valve 84 is rapidly switched, as by rotating internal elements clockwise ninety degrees as viewed in the diagram of FIG. 1. Effluent of the high temperature pyrolyzer 70 is then fed along a flow line 128 to combine with effluent of the low temperature pyrolyzer 98 and pass to the nitric oxide detector 80, which detects NO during the time interval tt2.

Figure 2:
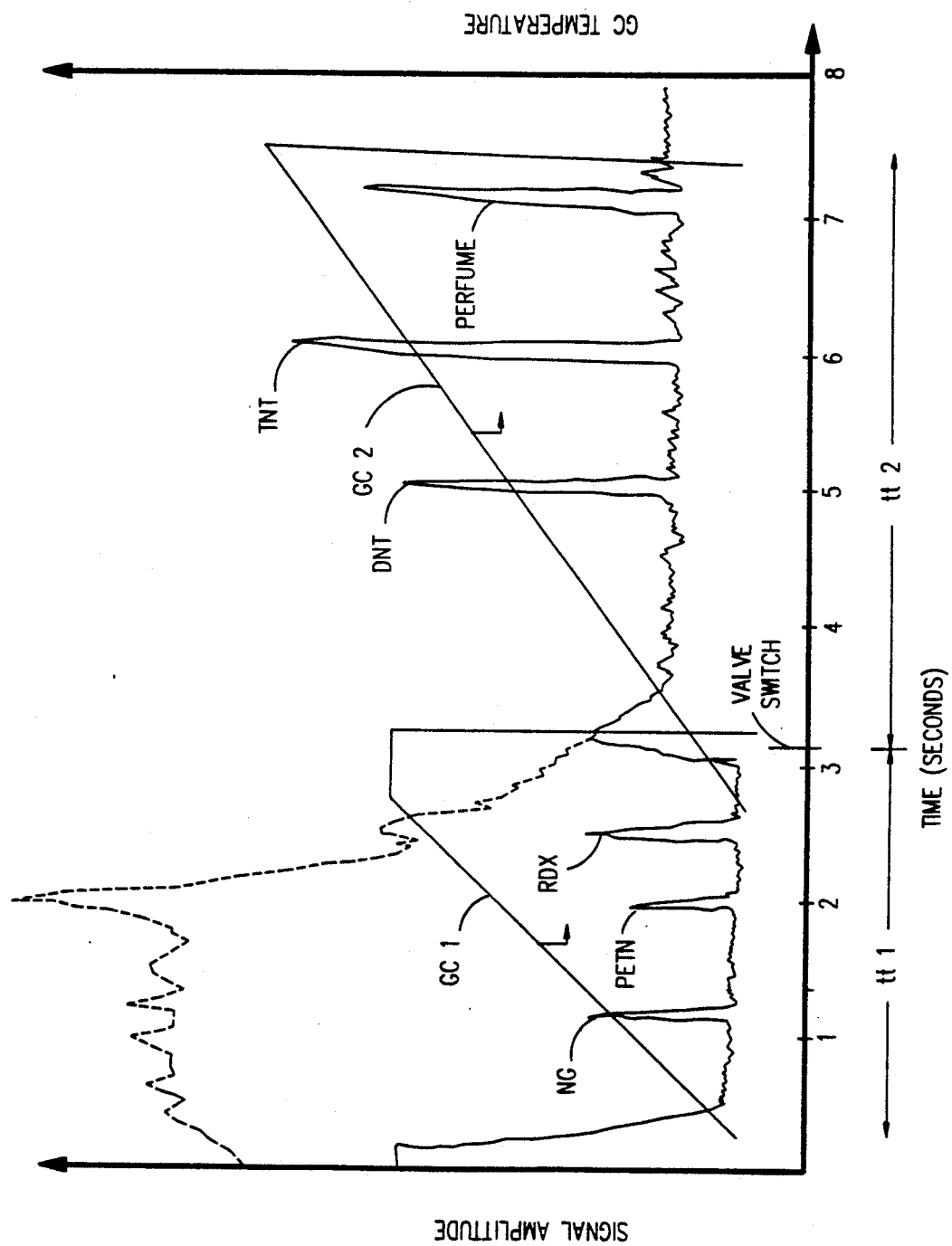
FIG. 2 is a sketch illustrating NO signals which would typically be produced in the vapor detection system of the invention.

FIG. 2 is a plot of signal amplitude versus time (chromatogram) from an output of the nitric oxide detector 80 which would typically result from an analysis in the vapor detection system 30 of a sample containing vapors of several explosives. The unbroken signal trace reflects output of the system 30 as shown in FIG. 1 while the dashed or broken signal trace reflects output which might typically have resulted during a first time interval tt1 from a system lacking the bypass branch 90 and the valve 84. The sketch also shows temperature ramps (labelled GC1 and GC2 and referenced to a temperature scale at right edge of FIG. 2) associated with typical operation of the first and second gas chromatographs 60 and 64 to achieve rapid separation and release of vapors from GC1 60 and GC2 64.

A comparison between the dashed signal and the unbroken signal of FIG. 2 during the first interval tt1 clearly illustrates the benefits of the bypass branch 90. Operation without the bypass branch 90 (dashed signal) yields a large ill-defined signal trace in which it is difficult to identify individual peaks because of the presence of many other compounds which are flowing through components downstream of GC1 60 undergoing decomposition in the high temperature pyrolyzer 70, and being detected as NO by the nitric oxide detector 80. Signals from compounds of interest, particularly those present in low concentration because their initial collection to form air samples was less favored due to low vapor pressures, may go undetected because they cannot be accurately identified. False alarms also may result.

A substantially cleaner signal (unbroken trace) is produced during the first time interval of detection (tt1) when sample analysis is performed using the system 30 which includes the bypass branch 90. Because the high temperature pyrolyzer 70 is avoided, the large ill-defined (broken) signal is replaced with a trace containing sharply-defined peaks of the explosives of interest (here NG and RDX). Hence the presence or absence of these compounds at predetermined times (detection windows) is easily monitored electronically and verified in chromatograms.

Other compounds of interest (e.g. explosives which are C-nitro compounds such as DNT and TNT) which do not decompose at the temperature of pyrolyzer 62 are detected during the second time interval tt2 following the switching of the valve 84 to direct effluent of the high temperature pyrolyzer 70 to the nitric oxide detector 80. As expected, at the beginning of tt2 the unbroken signal trace undergoes a "step" increase to merge with the broken signal trace upon switching of the valve 84. However, since by then most of the compounds not held in GC2 64 have passed through the system 30, the overall signal amplitude has decreased to a level at which individual peaks are readily distinguishable. Detection is also facilitated by the typically larger amplitudes of the DNT and TNT peaks associated with their higher concentrations (due to their higher vapor pressures—hence their ready collection in air samples). These higher peaks readily overcome a somewhat higher level of background signal and noise apparent in the tt2 portion of FIG. 2.

Figure 3:
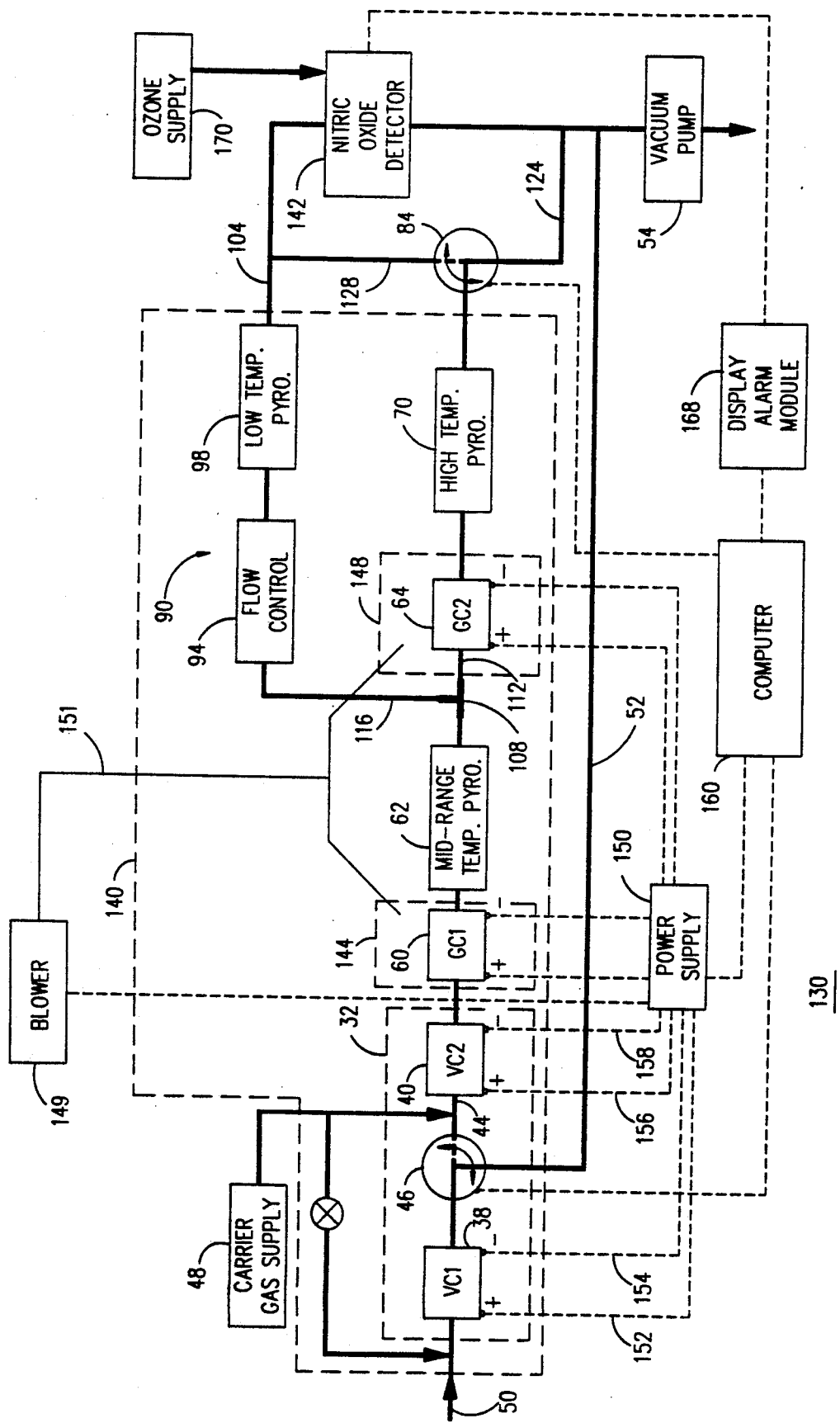
FIG. 3 is a block diagram of a vapor detection system according to a preferred embodiment of the invention such as that of FIG. 1 but showing additional components.

FIG. 3 is a block diagram illustrating some additional components which are included in a preferred embodiment of a vapor detection system 130 of the invention (In FIG. 3 components which are similar or the same as those of the system 30 of FIG. 1 are labelled with the same numerals). The system 130 (FIG. 3) includes an oven 140 enclosing all of the above-described components except the carrier gas supply 48, the valve 84, a chemiluminescence-based NO detector 142, and the vacuum pump 54. The oven 140, preferably an electric oven, provides a constant internal oven temperature at a level such that vapors readily flow without decomposition in a carrier gas along internal flow lines between components. A preferred temperature for the oven 140 for applications in which the system 130 is used in detecting explosives is about 180° C. This temperature matches a suitable temperature to be maintained in the low temperature pyrolyzer 98 so that a separate heater is not needed for the low temperature pyrolyzer 98. Two additional ovens 144 and 148 enclosing GC1 60 and GC2 64, respectively (or a single additional oven enclosing both), are also provided within the oven 140. The ovens 144 and 148 maintain GC1 60 and GC2 64 at a constant temperature (e.g., 95° C.), except during times when the temperatures of the gas chromatographs are rapidly increased to accelerate the removal of vapors.

One or more blowers or fans may also be included in the vapor detection system 130 to circulate ambient air over components at selected times—for example, blowers (not shown) within the ovens 144 and 148 and operated when the GC's are not being rapidly heated so as to maintain GC1 60 and GC2 64 at a uniform base temperature of about 95° C. A blower 149 may also be provided outside the ovens 140, 144, and 148 and operated for a few seconds following the rapid heating of the metal tubes of GC1 60 and GC2 64 to circulate ambient air along a duct 151 and over the metal tubes so as to hasten their cooldown.

One or more power supplies such as the power supply 150 is provided as part of the system 130 to provide electrical power for heating of components such as the vapor concentrators 38 and 40, GC1 60, GC2 64, and the pyrolyzers 62 and 70. The power supply 150 is electrically connected to both ends of the metal tube or sleeve of the vapor concentrators 38 and 40 (as indicated by broken lines 152, 154, 156, and 158) and is programmed under control of a computer 160 with one or more microprocessors to very rapidly (e.g., in one second) and precisely heat the metal sleeves so as to "fire" the vapors held by VC1 38 into VC2 40 and later to fire the vapors held by VC2 40 into GC1 60. The power supply 150 is also connected to metal tubes or sleeves encasing GC1 60 and GC2 64 to rapidly (e.g., within 2–4 seconds) heat these GC's. Other components controlled by the computer 160 include the two-position, high speed valve 84, the valve 46 between the VC1 38 and VC2 40, a display alarm module 168, and other valves controlling flows of gases such as carrier gas and ozone (supplied to the nitric oxide detector 142 if a chemiluminescence-based NO detector is used. In such a system a preferred method of producing ozone is by electrical discharge in an ozonator supplied by oxygen from electrolysis of water, with hydrogen from the electrolysis used as the carrier gas of the supply 48).

In operation of the vapor detection systems 30 and 130, vapors of gas samples to be analyzed are first concentrated or focussed in two steps as described above, by directing the gas sample through the vapor concentration unit 32. At a selected time after vapors have been trapped in the second vapor concentrator 40, and with a carrier gas continuously flowing through the system from the supply 48, the vapor concentrator 40 is very rapidly heated (e.g., in one second to a temperature of 250° C.) to release the vapors (substantially without decomposition) and inject them into GC1 60. Preferably heating of the vapor concentrator 40 (and of VC1 38 earlier to transfer vapors from VC1 38 to VC2 40) is controlled to obtain desired temperatures by monitoring the resistance of its metal sheath (e.g., by utilizing measurements of the voltage drop which occurs along the tube when a small sensing current is periodically applied or due to the heating current). A preferred heating control is described below. Also, at or prior to the time of firing of the vapor concentrator 40, the valve 84 is set in position to vent effluent from the high temperature pyrolyzer 70 directly through the vacuum pump 54. Shortly thereafter, GC1 60 is rapidly heated (e.g., in ramplike fashion in about 2-3 seconds to a temperature of about 300° C.) to quickly move vapors in timewise-separated fashion out of GC1 60 and then into and through the mid-range temperature pyrolyzer 62. As the vapors with carrier gas travel rapidly through the pyrolyzer 62, nitrate esters and nitramines among the vapors are decomposed to produce NO and $NO_2$, while other compounds such as C-nitro compounds (e.g., DNT, TNT) remain intact.

After emerging from the mid-range temperature pyrolyzer 62, the gas sample is split into two portions by the "T" connection 108, with one portion flowing into GC2 64 and the remainder through the flow line 116 and along the remainder of the bypass branch 94 into the nitric oxide detector 80 or 142. The fractional split of the flow is determined primarily by the flow resistances of the various components downstream of the T 108, including that of the flow controller 94. Since higher detection responses are generally obtainable with higher fractions of flow, the effluent of the mid-range temperature pyrolyzer 62 may be divided so that more than half is delivered to the bypass branch 90 if the specific compounds to be detected from the portion of the branch 90—i.e., during time interval tt1—are typically present in the gas sample in smaller amounts (e.g., less is present in a collected sample due to lower vapor pressure) than are compounds to be detected in interval tt2. For example, seventy percent of the flow may be directed through the bypass branch 90, with the remaining thirty percent passing into GC2 64.

As the gas sample flows rapidly through the bypass branch 90, NO remains unchanged, $NO_2$ is reduced to NO in the low temperature pyrolyzer 98, and other nitrogen-containing compounds are not decomposed to yield NO or $NO_2$. (In particular, compounds which would decompose to produce NO if passed through the high temperature pyrolyzer 70 remain intact so as not to yield potential interferences and ircreased background noise signals.) The nitric oxide detector 80 or 142 then quickly detects NO, producing signals at specific times during the interval tt1 which are identifiable as one or more specific compounds of interest. Timewise plots or chromatograms of the signals are automatically generated and indicator lights or other alarms may be triggered in response to the signals.

The fraction of gas sample which is directed to GC2 64 instead of to the bypass branch 90 has vapors which had been selectively retained in GC1 62 and these vapors, upon entering GC2 64, begin separating and migrating through GC2 64. The carrier gas, and any NO and $NO_2$ in the fraction of gas sample applied to GC2 64, pass rapidly through GC2 64 and the high temperature pyrolyzer 70 and during time interval tt1 are vented through the vacuum pump 54 and not used for detection. At the end of the time interval tt1, or shortly prior to this, and prior to the time at which separable vapors would emerge from GC2 64 by migration at its normal operating temperature, the valve 84 is switched so that effluent from the high temperature pyrolyzer 70 passes through the flow line 128 and combines with the flow from the bypass branch 90 to enter the nitric oxide detector 80 or 142. During this time interval tt2 heating of GC2 64 quickly moves vapors from GC2 64 in timewise-separated fashion into and through the high-temperature pyrolyzer 70. As the vapors rapidly travel through the high temperature pyrolyzer 70, certain nitrogen-containing compounds such as C-nitros are decomposed to yield NO. Almost immediately thereafter detection signals indicative of these compounds are produced in the NO detector 80 or 142.

The result of the above-noted operating steps is detection of specific compounds which are nitramines and nitrite esters during a first time interval of detection (tt1) and detection of other specific nitro-compounds (C-nitros) during a second time interval of detection (tt2), with typical total detection time of about ten seconds or less. In the preferred vapor detection systems 30 and 130 operated to detect vapors of certain nitrogen-based explosives present in gas samples, nitroglycerin, EGDN, PETN, and RDX may be detected in the first time interval, and DNT and TNT are detected in the second time interval. Because the portion of each sample analyzed during the first time interval does not pass through a high temperature pyrolyzer, interferences and background noise associated with decomposition products of this pyrolyzer are avoided during the first time interval. Also, because of the use of GC2 64 (and its time of heating) and the high temperature pyrolyzer 70, vapors of C-nitros (e.g., DNT and TNT) are time-shifted (delayed) and their signals better-separated from signals of other compounds (e.g., NG, PETN, and RDX) to be detected. The vapor detection system and method of the invention thus retain the benefits of time-shifting of signals in enhancing the timewise separation of specific compounds while avoiding additional potential interferences and improving sensitivity of detection during the first time interval.

Figure 4:
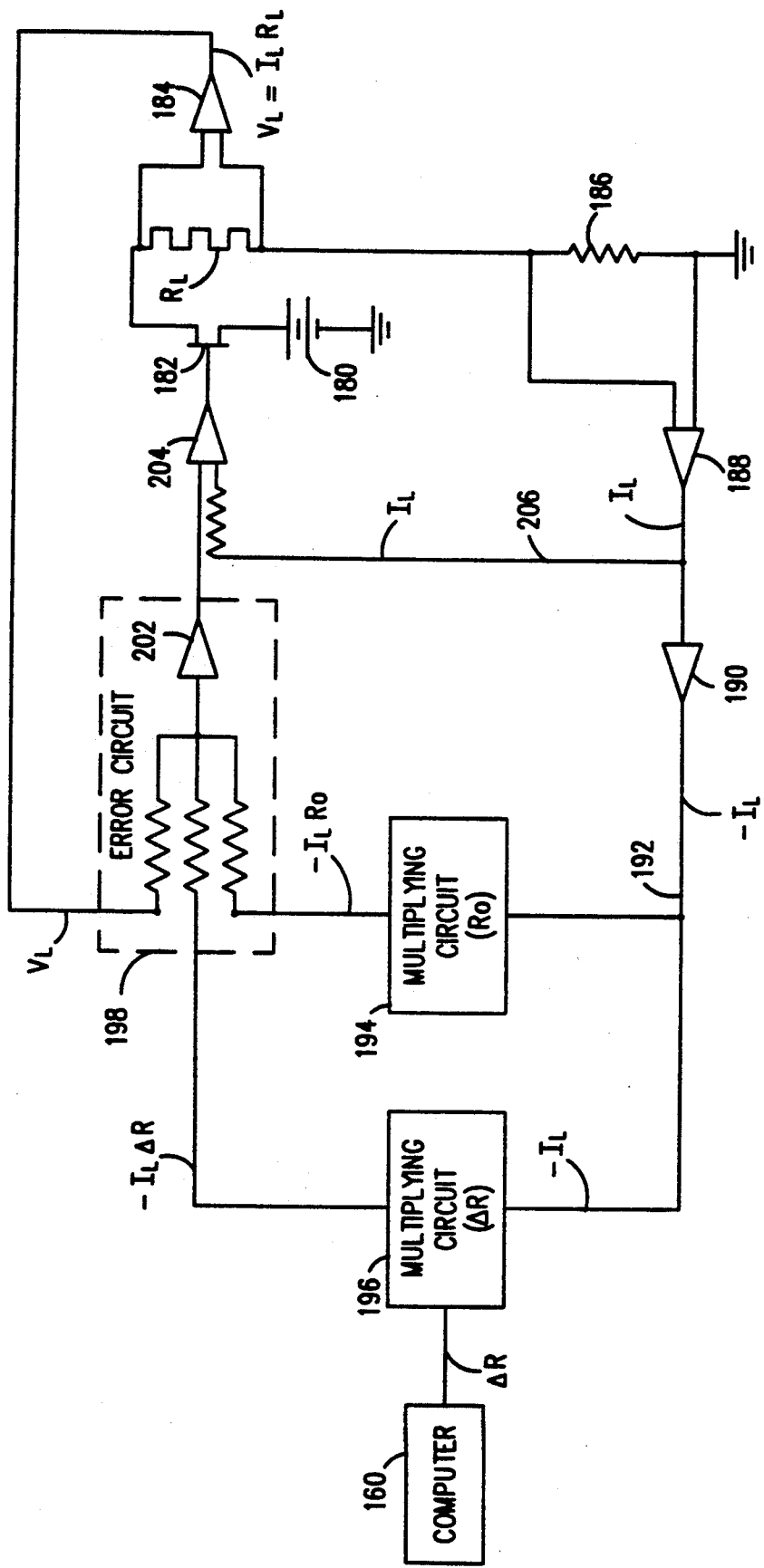
FIG. 4 is a schematic diagram of an electrical circuit for rapid, precise control of temperature, as in certain vapor concentrators and gas chromatographs of a vapor detection system of the invention.

A feature of the present invention resides in the manner in which the vapor concentrators VC1 38 and VC2 40 and the chromatographs GC1 60 and GC2 64 are heated to precise temperatures as indicated above. FIG. 4 shows a schematic circuit diagram of such an arrangement.

In this arrangement, heating is supplied by passing current through the metal (e.g., stainless steel) tubes forming the outer casings for the concentrators VC1 38 and VC2 40 and GC1 60 and GC2 64. As is well known, such metals increase in resistance with temperature. To set each of VC1 38, VC2 40, GC1 60 and GC2 64 at a desired temperature, current is supplied at one end of its tube to flow through the length of the tube to the other end, which heats the tube and increases its resistance. The resistance is sensed from the current and voltage and compared with the known resistance corresponding to the desired temperature. Stored in the computer 160 for each value of temperature is a known value of resistance of the tube of VC1 38, VC2 40, GC1 60 and GC2 64, which may be determined by measurement or computation. For convenience, the stored resistance value may be the computed change in resistance from a base value $R_o$ determined at a base temperature, such as room temperature or 10° C., for example. Each time a change in temperature is desired, the circuit changes the current to adjust the tube resistance to the value of resistance corresponding to the desired temperature at that instant. The system thereby permits profiling the variation of tube temperature with time in any desired manner by programming into the computer 160 the timed sequence of resistances to be obtained (e.g., resistance values at 10 millisecond intervals). This is accomplished by the circuit of FIG. 4.

In FIG. 4 the tube resistance is represented by load $R_L$. Current, as from power supplied by a battery 180, is passed through load $R_L$ under control of a power transistor (e.g. FET) 182. The voltage across $R_L$ is passed through an amplifier 184, whose output represents that voltage $V_L$, which equals $R_L \times I_L$, where $I_L$ is the load current. A small value (e.g. 0.1 ohm) resistor 186 is in series with load $R_L$. The voltage across resistor 186 represents the value of current $I_L$ and is supplied to an amplifier 188 whose output is representative of the load current $I_L$. The $I_L$ signal is inverted by an inverter 190 to provide on lead 192 a signal representative of $-I_L$. That signal is passed through a gain or multiplier circuit 194 to provide an output representing $-I_L \times R_o$ where $R_o$ is the fixed base resistance of the load (i.e., tube), as at room temperature.

The $-I_L$ signal from inverter 190 is also supplied to a multiplying circuit 196 (e.g. a multiplying DAC) which also receives a signal $\Delta R$ from computer 160. Signal $\Delta R$ represents the increment of resistance (over the base resistance $R_o$) for the load tube when it has attained the desired temperature, at the moment the $\Delta R$ signal is received by circuit 196. As indicated above, the computer 160 periodically (e.g. every 0.01 seconds) determines what $\Delta R$ is needed at that moment to correspond to the desired temperature.

The multiplying circuit 196 thus provides an output representing $-I_L \times \Delta R$. This output is summed with the $V_L$ signal from amplifier 184 and the $-I_L \times R$ signal from circuit 194 in an error circuit 198 comprising a summing network 200 and an error amplifier 202, whose error signal output represents $V_L - I_L(R_o + \Delta R)$. To make $R_L = R_o + \Delta R$, the output of error amplifier 202 is fed through an amplifier 204 to control transistor 182 to change $I_L$ by the amount required for the current heating effect on the load tube $R_L$ to change the tube resistance by the necessary amount to cause the error signal output from error amplifier 202 to become zero; i.e., $R_L$ then equals $R_o + \Delta R$. The gain of the loop containing amplifiers 202, 204, and 184 is made very high and may be of the order of one million. An $I_L$ signal from amplifier 188 is applied over lead 206 to an input to amplifier 204 so that power transistor 182 will maintain current $I_L$ even for zero error signal (to maintain resistance sensing even when a change in heating power is not required).

In this way, the system specifies the tube resistance $R_L = R_o + \Delta R$ for the desired tube temperature, and adjusts the current flowing along the tube to heat the tube to attain the resistance, at which time the temperature is as desired. With the small mass of the tube, this arrangement permits extremely accurate and rapid creation of tube temperature, which may be varied precisely according to a desired time profile such as that of GC1 60 and GC2 64 in FIG. 2 or as described above as to VC1 38 and VC2 40. For reduction of temperature, transistor 182 shuts off current, and the tube may cool naturally or under the influence of air blown over the tube. It will be understood that this resistance-determined arrangement may be used whenever rapid and precise temperature control is desired.

The above-described embodiments are intended as illustrative and non-limiting, and other embodiments are readily apparent. For example, the effluents of both the high temperature and low temperature pyrolyzers may be separately controlled by valves and these effluents need not be combined during the second time interval of detection. The low temperature pyrolyzer 98 may be eliminated in certain systems—e.g., systems for detecting nitrogen-containing compounds in which nitric oxide sufficient for detection of a first set of compounds is produced from decomposition of compounds in the mid-range temperature pyrolyzer 62. Also, the valve 84 may be eliminated if a separate NO detector, or separate chamber of a dual-chamber NO detector, is employed to detect NO in each of the effluents. Moreover, the tubes for the vapor concentrators and gas chromatographs may be of a form different from the capillary quartz GC tube threaded through needlestock metal (e.g., stainless steel) tube so long as the tube systems have a small diameter flow channel near a suitable coating of GC material which can be rapidly and precisely heated. One alternative is a small diameter metal tube along whose interior wall quartz or glass material has been deposited and then lined with a coating of GC material. Another tube system is a quartz capillary GC tube having a standard commercially applied thin outer coating (e.g., aluminum) to protect and facilitate coiling of the tube for GC applications, with a less oxidizable, durable overlay coating (e.g, nickel) on the aluminum for conducting current for electrical heating, and with a coating of GC material within the tube. The invention is defined by the claims which follow and includes all embodiments and their equivalents within the scope of the claims.

What is claimed is:

1. A method of controlling the temperature of a current-carrying element whose resistance varies with temperature, comprising the steps of:

supplying a current through said element, deriving a voltage signal representing the voltage across said element, deriving a current signal representing the current through said element, inverting said current signal to form an inverted current signal, storing a plurality of resistance signals each representing the value of resistance of said element at an individual predetermined temperature, selecting a resistance signal corresponding to a desired temperature, computing a resistance increment signal as the difference between said resistance signal and a base resistance signal corresponding to a fixed base temperature of said element, deriving a first product signal by multiplying said resistance increment signal by said inverted current signal, deriving a second product signal by multiplying said inverted current signal by said base resistance signal, deriving an error signal by summing (a) said first product signal, (b) said second product signal, and (c) said voltage signal, and amplifying the sum of said signals, combining said error signal with said current signal to derive a combined signal, and controlling the current through said element with said combined signal to minimize said error signal.

2. A method as in claim 1 further comprising:
sequentially selecting resistance signals corresponding to temperatures of a predetermined temperature characteristic,
whereby said element is caused to vary in temperature according to said characteristic.

3. A method as in claim 1 further comprising:
periodically changing said selected resistance signal in correspondence with temperatures of a desired temperature vs. time profile,
whereby the temperature of said element is varied with time in accordance with said profile.

4. A method as in claim 3 wherein said change occurs as rapidly as of the order of 0.01 second.

5. A method as in claim 2 wherein said element comprises a metal tube or a metal coating applied to a non-metallic tube, and said sequential selection includes selecting resistance signals according to a temperature characteristic which results in the flash-heating of said element to a predetermined elevated temperature for a selected interval of time.

6. A method as in claim 2 wherein said element comprises a metal tube or a metal coating applied to a non-metallic tube, either said tube forming part of a gas chromatograph, and said sequential selection includes selecting resistance signals which result in the heating of said element to a predetermined elevated temperature during a time interval of less than about five seconds according to a ramplike temperature characteristic.

7. Apparatus for controlling the temperature of a current-carrying element whose resistance varies with temperature, comprising:
a variable-current source for supplying current through said element,
a voltage-signal circuit coupled across said element to derive a voltage signal representing the voltage across said element,
a small-value resistor in series with said element,
a current-signal circuit coupled to said resistor to derive a current signal representative of the current through said element, said current-signal circuit including an inverter for inverting said current signal to derive an inverted current signal,
a source of resistance signals, each representing the difference between the resistance of said element at a respective temperature of said element and a fixed base resistance,
a first multiplying circuit coupled to said resistance signal source and said current-signal circuit to derive a first product signal representing the product of a resistance signal corresponding to a desired temperature of said element and said inverted current signal,
a second multiplying circuit coupled to said inverter to derive a second product signal representing the product of said inverted current signal and a base resistance signal corresponding to a fixed base temperature,
an error circuit coupled to said multiplying circuits and said voltage-signal circuit, said error circuit including a summing network to derive a summed signal as the sum of said product signals and said voltage signal, and
high-gain amplifying means for amplifying said summed signal, said high-gain amplifying means being coupled to said variable-current source to vary said current supplied to said element in manner such that said element is caused to attain said desired temperature.

8. A method of controllably varying, at predetermined intervals as short as 0.01 seconds, the temperature of a current-carrying element whose resistance varies with temperature, according to a predetermined temperature characteristic, comprising the steps of:
storing a plurality of resistance signals each representing the value of resistance of said element at an individual predetermined temperature, including as one of said stored signals a base resistance signal representing the resistance of said element at a fixed base temperature;
applying electrical power from a power source to said element so as to pass a current through said element;
establishing a desired temperature of said element by:
(a) deriving a current signal representing the current passing through said element,
(b) inverting said current signal to derive an inverted current signal,
(c) deriving a voltage signal representing the voltage across said element,
(d) from said plurality of stored resistance signals, selecting a resistance signal corresponding to said desired temperature,
(e) multiplying said inverted current signal by the difference between said selected resistance signal and said base resistance signal to form a first product signal,
(f) multiplying said base resistance signal by said inverted current signal to form a second product signal,
(g) summing said first product signal, said second product signal, and said voltage signal and amplifying said sum to form an error signal,
(h) combining said error signal and said current signal to derive a combined signal, and
(i) applying said combined signal to said element in a manner to control the current passing through said element to minimize said error signal and thereby achieve said desired temperature; and
repeating steps (a) through (i) at said predetermined intervals to vary the temperature of said element according to said predetermined temperature characteristic.

* * * * *